(12) United States Patent
Xu et al.

(10) Patent No.: US 8,198,312 B2
(45) Date of Patent: Jun. 12, 2012

(54) COMPOSITIONS AND METHODS OF MAKING A PHOTOACTIVE AGENT

(75) Inventors: Leon Xu, Issaquah, WA (US); Alexander J. Pallenberg, Duvall, WA (US)

(73) Assignee: Light Sciences Oncology, Inc., Snoqualmie, WA (US)

( * ) Notice: Subject to any disclaimer, the term of this patent is extended or adjusted under 35 U.S.C. 154(b) by 697 days.

(21) Appl. No.: 11/772,024

(22) Filed: Jun. 29, 2007

(65) Prior Publication Data

US 2008/0021210 A1 Jan. 24, 2008

Related U.S. Application Data

(60) Provisional application No. 60/817,769, filed on Jun. 30, 2006.

(51) Int. Cl.
*A61K 31/409* (2006.01)
(52) U.S. Cl. .................................................. 514/410
(58) Field of Classification Search .................. 540/145
See application file for complete search history.

(56) References Cited

FOREIGN PATENT DOCUMENTS

| EP | 0 200 218 | 11/1986 |
| EP | 0629409 A | 12/1994 |

OTHER PUBLICATIONS

Hargus, J., et al., "Mono-(L)-aspartylchlorin-$e_6$," *Photochemistry and Photobiology*, 83: 1-10, 2007.
Hargus, J., "Naturally-Derived Porphyrin and Chlorin Photosensitizers for Photodynamic Therapy," The Department of Chemistry, Louisiana State University, 2005, pp. 1-69.

*Primary Examiner* — James O Wilson
*Assistant Examiner* — Brian McDowell
(74) *Attorney, Agent, or Firm* — Seed IP Law Group PLLC

(57) ABSTRACT

A composition of matter of an anhydride of formula 1 below and an improved two stage reaction process for production of mono-L-aspartyl chlorin $e_6$, utilizing the anhydride:

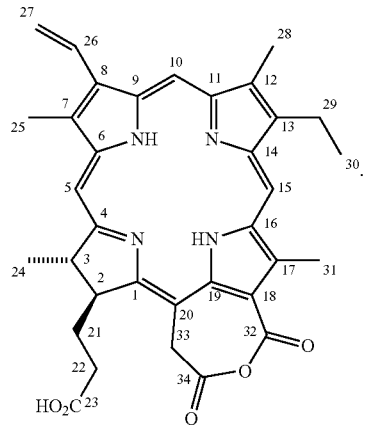

4 Claims, 9 Drawing Sheets

COMPOSITIONS AND METHODS OF MAKING A PHOTOACTIVE AGENT

CROSS-REFERENCE TO RELATED APPLICATION

This application claims the benefit under 35 U.S.C. §119 (e) of U.S. Provisional Patent Application No. 60/817,769 filed Jun. 30, 2006, which provisional application is incorporated herein by reference in its entirety.

BACKGROUND

1. Technical Field

This disclosure generally relates to the field of bio-affecting and body treating compositions and, more particularly, to photo-active compounds, composition, and methods useful in the detection, prevention, and/or treatment of, for example, cancerous tissues.

2. Description of the Related Art

Mono-L-aspartyl chlorin $e_6$ tetra sodium salt is commonly known as Talaporfin Sodium, and is known to be a photoactive chemical or drug. For example, U.S. Pat. No. RE 37,180 relates to methods of using mono-L-aspartyl chlorin $e_6$ that broadly include intravenous administration of the drug to a patient and applying light of an appropriate wave length to tissue containing the drug, to photo-activate the drug. Once activated, the drug occludes new blood vessels. Accordingly, the drug is useful in the treatment of diseases where blood vessel occlusion is expected to have a positive effect.

Talaporfin Sodium is typically produced from plant raw material. During the process, which includes both extraction and reaction steps, byproducts are produced. One of these byproducts is di-L-aspartyl chlorin $e_6$. While diaspartyl chlorin $e_6$ occurs as a reaction byproduct in relatively low quantity, typically about 5% in well controlled processes, it requires stringent processing for removal to purify the Talaporfin Sodium product to acceptable standards. For example, purifying a crude Talaporfin Sodium reaction product and/or removing various impurities (e.g., diaspartyl chlorin $e_6$) usually requires subjecting a reaction product to multiple HPLC (high performance liquid chromatography) steps to achieve an acceptable Talaporfin Sodium purity level. This purification procedure is expensive and time consuming, and may also lead to a substantial loss, up to about 50%, of the Talaporfin Sodium along with the removed impurities.

Accordingly, it is desirable to develop a process that produces a Talaporfin Sodium product without the expensive repetitive purification steps or with fewer processing steps. In addition, it is desirable to purify the reaction product without loss of a large proportion of the Talaporfin Sodium, and/or to maintain or increase the yield of Talaporfin Sodium product per mass of raw material input.

Commercial acceptance of Talaporfin Sodium is dependent on a variety of factors, such as cost to manufacture, shelf life, stability during storage, ease-of manufacture, efficacy, bioavailability, pharmacokinetic properties, etc. Therefore, it is desirable to have novel approaches of making Talaporfin Sodium that significantly reduce the manufacturing cost. It is also desirable to have novel compositions that result in purer forms of Talaporfin Sodium.

The present disclosure is directed to overcoming one or more of the shortcomings set forth above, and providing further related advantages.

BRIEF SUMMARY

In one aspect, the present disclosure is directed to a chemical reaction product of chlorin $e_6$ and a carbodiimide. In some embodiments, the chemical reaction product comprises a chlorin $e_6$ anhydride of the form:

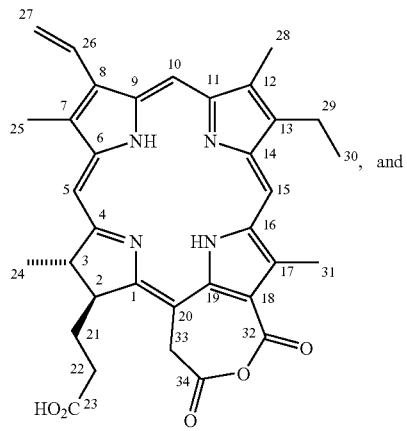
and precursors of diaspartyl chlorin $e_6$. In some embodiments, the precursors of diaspartyl chlorin $e_6$ comprise less than about 5 mol % based on the total chlorin species present within the chemical reaction product.

In another aspect, the present disclosure is directed to a composition, comprising a compound of Formula I

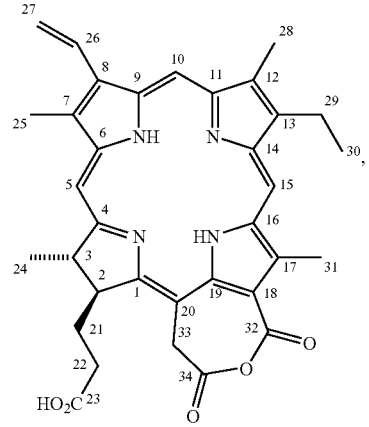

Formula I or a pharmaceutically acceptable salt thereof, in a substantially pure form.

In another aspect, the present disclosure is directed to a process for preparing a chlorin $e_6$ anhydride, or a pharmaceutically acceptable salt thereof. The process includes combining chlorin $e_6$ with a carboxyl activating agent to obtain a mixture comprising a chlorin $e_6$ anhydride having the following formula

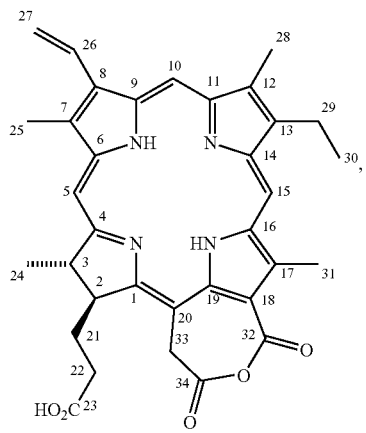

or a salt thereof.

The process may further include purifying the chlorin $e_6$ anhydride, or salt thereof.

In another aspect, the present disclosure is directed to a method for preparing an intermediate. The method includes activating chlorin $e_6$ with a carboxyl activating agent to obtain a mixture including an intermediate, the intermediate exhibiting a spectrum comprising chemical shifts in ppm at about 1.63 (t, 3H), 1.72/2.05 (m, 2H), 1.78 (d, 3H), 2.50/2.65 (m, 2H), 3.14 (s, 3H), 3.42 (s, 3H), 3.68 (br. q, 2H), 3.69 (s, 3H), 4.63 (br. q, 1H), 4.67 (br. d, 1H), 5.59/5.56 (d, 2H), 6.37/6.16 (d, 1H), 8.07 (dd, 1H), 8.86 (s, 1H), 9.35 (s, 1H), and 9.67 (s, 1H) when analyzed using proton nuclear magnetic resonance ($^1$H-NMR) spectroscopy, at 500 MHz, using a solvent comprising $d_6$-acetone and $d_6$-dimethyl sulfoxide. The method further includes isolating the intermediate.

In another aspect, the present disclosure is directed to a method for preparing Talaporfin Sodium, or a pharmaceutically acceptable salt thereof. The method includes combining an aspartate salt composition having a pH ranging from about 10 to about 12 with a chemical reaction product according to claim 1 in the presence of an organic solvent to form a reaction mixture. The method may further include rendering the reaction mixture basic. The method may further include precipitating the Talaporfin, or a pharmaceutically acceptable salt thereof, from the basic reaction mixture.

In another aspect, the present disclosure is directed to a method of preparing Talaporfin Sodium. The method includes utilizing a purified intermediate reaction mixture in a reaction to prepare Talaporfin Sodium, the purified intermediate reaction mixture having been obtained from a crude reaction mixture comprising chlorin $e_6$, a chlorin $e_6$ anhydride, and precursors of diaspartyl chlorin $e_6$ from which a significant proportion of the precursors of diaspartyl chlorin $e_6$ has been removed.

In another aspect, the present disclosure is directed to a reaction product, comprising a product of a coupling reaction between a first reaction volume and a second reaction volume, the first reaction volume comprising a chlorin $e_6$ anhydride of the formula

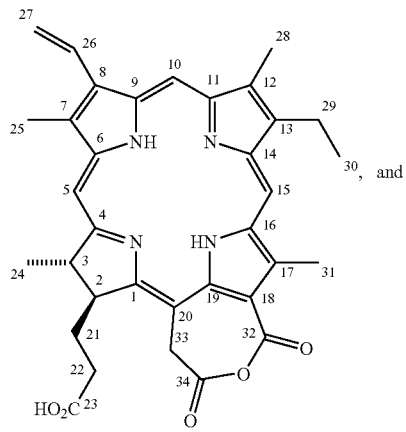

less than about 5 mol % precursors of diaspartyl chlorin $e_6$ based on total chlorin species within the reaction product; and the second reaction volume comprising L-aspartic acid or ester thereof. In some embodiments, the reaction product comprises mono-L-aspartyl chlorin $e_6$, or a pharmaceutically acceptable salt thereof, and diaspartyl chlorin $e_6$. Examples of chlorin species include chlorin $e_6$, a chlorin $e_6$ anhydride, and precursors of diaspartyl chlorin $e_6$, and the like, as well as compounds comprising a chlorin chromophore.

In another aspect, the present disclosure is directed to a process for preparing mono-L-aspartyl chlorin $e_6$, or a pharmaceutically acceptable salt thereof. The process includes combining chlorin $e_6$ with a carboxyl activating agent to obtain a mixture comprising a Formula I intermediate Formula I

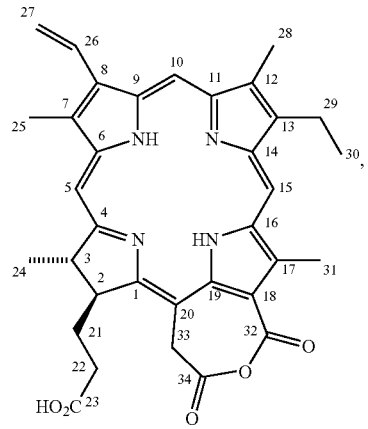

or a salt thereof. The process further includes isolating the Formula I intermediate, or salt thereof. In some embodiments, the process further includes combining the isolated Formula I intermediate, or salt thereof, with an amine-containing reagent to form Talaporfin Sodium, or a pharmaceutically acceptable salt thereof.

In another aspect, the present disclosure is directed to a process for preparing a photoactive agent, or a pharmaceutically acceptable salt thereof. The process includes combining a composition comprising a compound of the formula

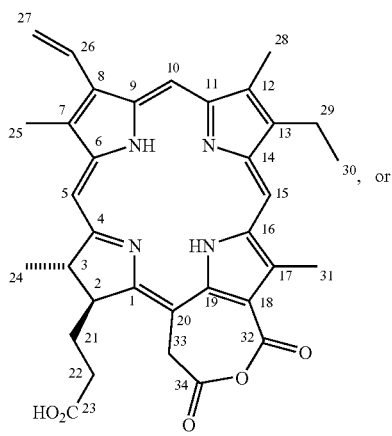

a pharmaceutically acceptable salt thereof, an organic solvent, and one or more of diaspartyl chlorin $e_6$ precursors, with a basic aqueous sodium aspartate composition to form a crude mono-L-aspartyl chlorin $e_6$ reaction mixture. In some embodiments, the crude reaction mixture comprises less than about 2 mol % diaspartyl chlorin $e_6$ based on the total chlorin species present within the crude reaction mixture. The process further includes making the reaction mixture basic. In some embodiments, the process further includes precipitating a substantial amount of the mono-L-aspartyl chlorin $e_6$ from the reaction mixture.

In another aspect, the present disclosure is directed to a chemical reaction product of chlorin $e_6$ and a dehydration agent, the chemical reaction product comprising a chlorin $e_6$ anhydride of the form:

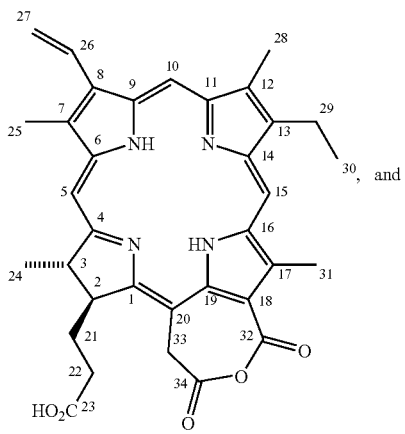

precursors of diaspartyl chlorin $e_6$. In some embodiments, the precursors of diaspartyl chlorin $e_6$ comprise less than about 5 mol % based on the total chlorin species present within the chemical reaction product.

In another aspect, the present disclosure is directed to a mixture that includes a reaction product of chlorin $e_6$. The mixture includes the previously unknown chlorin $e_6$ an hydride, and/or derivatives thereof. The chlorin $e_6$ anhydride is of the formula:

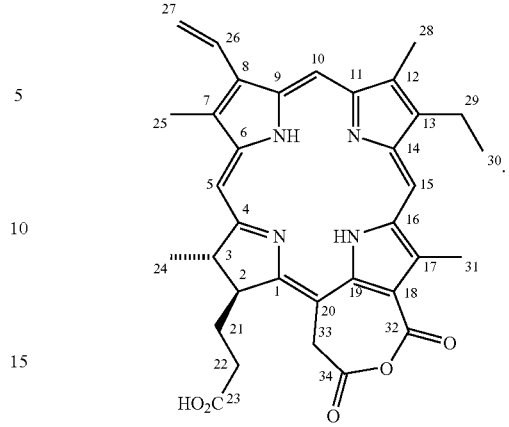

The mixture has a significantly reduced concentration of precursors of diaspartyl chlorin $e_6$ and other unwanted species, typically less than 5% based on total chlorin species present.

The mixture may be a purified reaction product of an activation reaction of chlorin $e_6$ with a carbodiimide. The carbodiimide may be N-ethyl-N'-(3-dimethylaminopropyl)-carbodiimide hydrochloride (EDC) or N,N'-dicyclohexyl-carbodiimide (DCC).

In some embodiments, the chlorin $e_6$ anhydride of the above formula may be in a mixture that has up to about 5% of precursors of diaspartyl chlorin $e_6$ based on the total chlorin species in the reaction mixture. In another, the chlorin $e_6$ anhydride might be in a mixture that contains up to 3% diaspartyl chlorin $e_6$ precursors based on the total chlorin species in the mixture.

In another aspect, the present disclosure is directed to a method of preparing Talaporfin Sodium that includes the steps of: preparing an intermediate reaction mixture including chlorin $e_6$, the anhydride thereof, and precursors of diaspartyl chlorin $e_6$; purifying the mixture by removing a significant proportion of the precursors of diaspartyl chlorin $e_6$ from the mixture; and utilizing the purified mixture in a reaction to prepare Talaporfin Sodium.

In some embodiments, the intermediate reaction mixture may include dimethyl sulfoxide. In some embodiments, the intermediate reaction mixture may include (EDC) and dimethyl formamide (DMF). The purifying step may include filtering through a bed of activated silica.

The purifying step may also include adding agents designed to suppress the formation of precursors to di-L-aspartyl chlorin $e_6$ and other unwanted species. The purifying step may include removal of diaspartyl chlorin $e_6$ precursors to a concentration of less than about 5% or less than about 3% based on the total chlorin species present in the intermediate reaction mixture.

The utilizing step may include coupling at high pH in dimethyl sulfoxide with L-aspartic acid or a derivative or ester thereof. The utilizing may also include coupling with L-aspartic acid or a derivative or ester thereof in an aqueous alkaline solution.

In another aspect, the present disclosure is directed to a reaction product that includes: the product of a coupling reaction between a first reaction volume comprising less than about 5% (based on total chlorin species present) of precursors of diaspartyl chlorin e6, the first reaction volume comprising a chlorin $e_6$ anhydride of the formula:

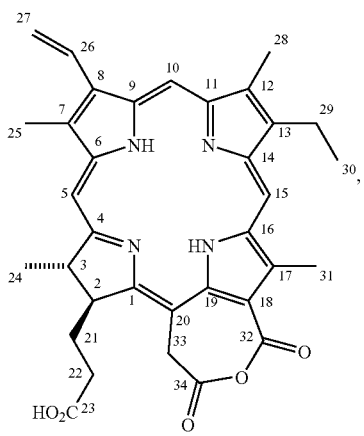

and a second reactant comprising L-aspartic acid, or a derivative or ester thereof.

The reaction product may include up to about 1% diaspartyl chlorin $e_6$ based on total chlorin species present. The first reaction volume may include dimethyl sulfoxide. The first reaction volume may be purified to remove precursors of diaspartyl chlorin $e_6$ and other unwanted reaction products by a suitable separation process, such as filtration through a bed of activated silica, and the like.

In yet another aspect, the present disclosure is directed uses of a purified chlorin $e_6$ anhydride as an intermediate in the preparation of compounds comprising chlorin $e_6$ linked via a peptide bond to other chemical moieties.

BRIEF DESCRIPTION OF THE DRAWINGS

A more complete understanding of the present disclosure may be obtained by referring to the detailed description and claims when considered in conjunction with the following Figures, wherein like reference numbers refer to similar elements throughout the Figures.

DETAILED DESCRIPTION

Figure 1:
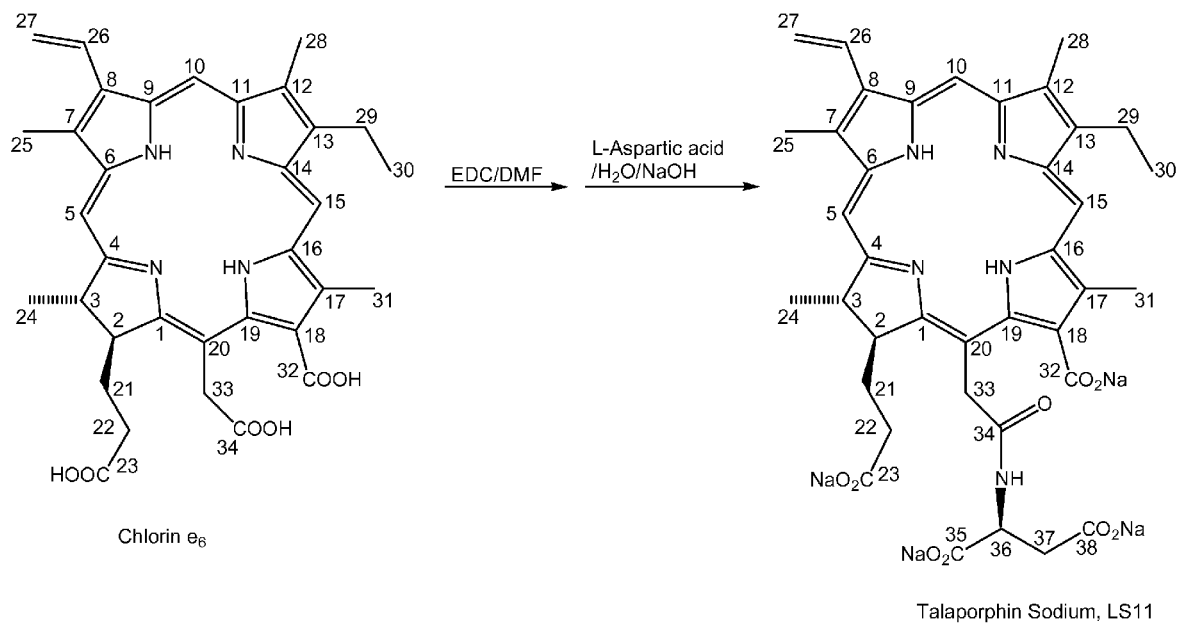
FIG. 1 is schematic depiction of a two stage process (activation followed by coupling) for synthesizing Talaporfin Sodium from chlorin $e_6$ according to one illustrative embodiment.
Figure 2A:
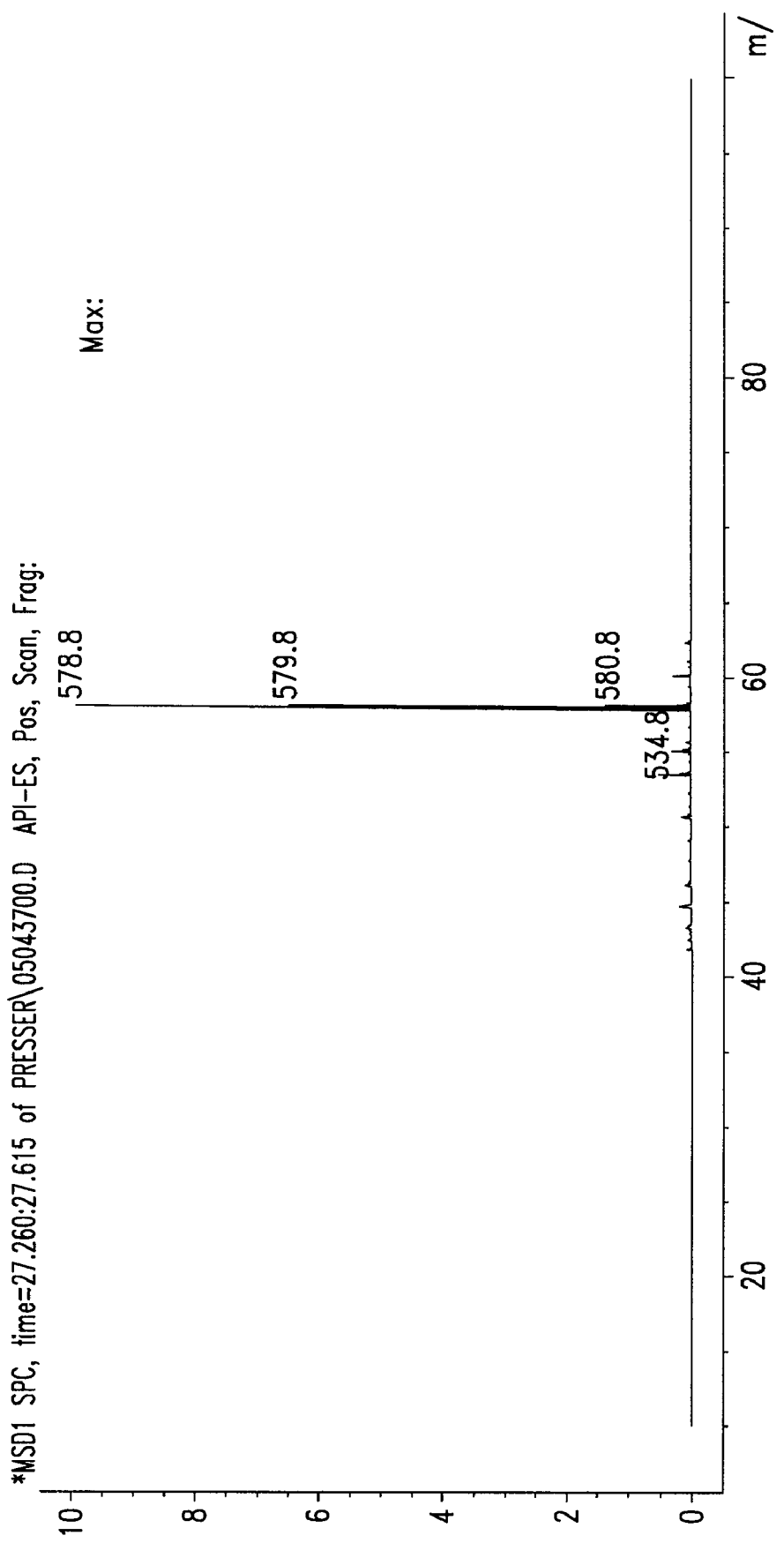
FIG. 2A is a relative intensity versus mass-to-charge ratio (m/z) mass spectrometry analysis plot of a purified chlorin $e_6$ anhydride composition according to one illustrative embodiment.
Figure 2B:
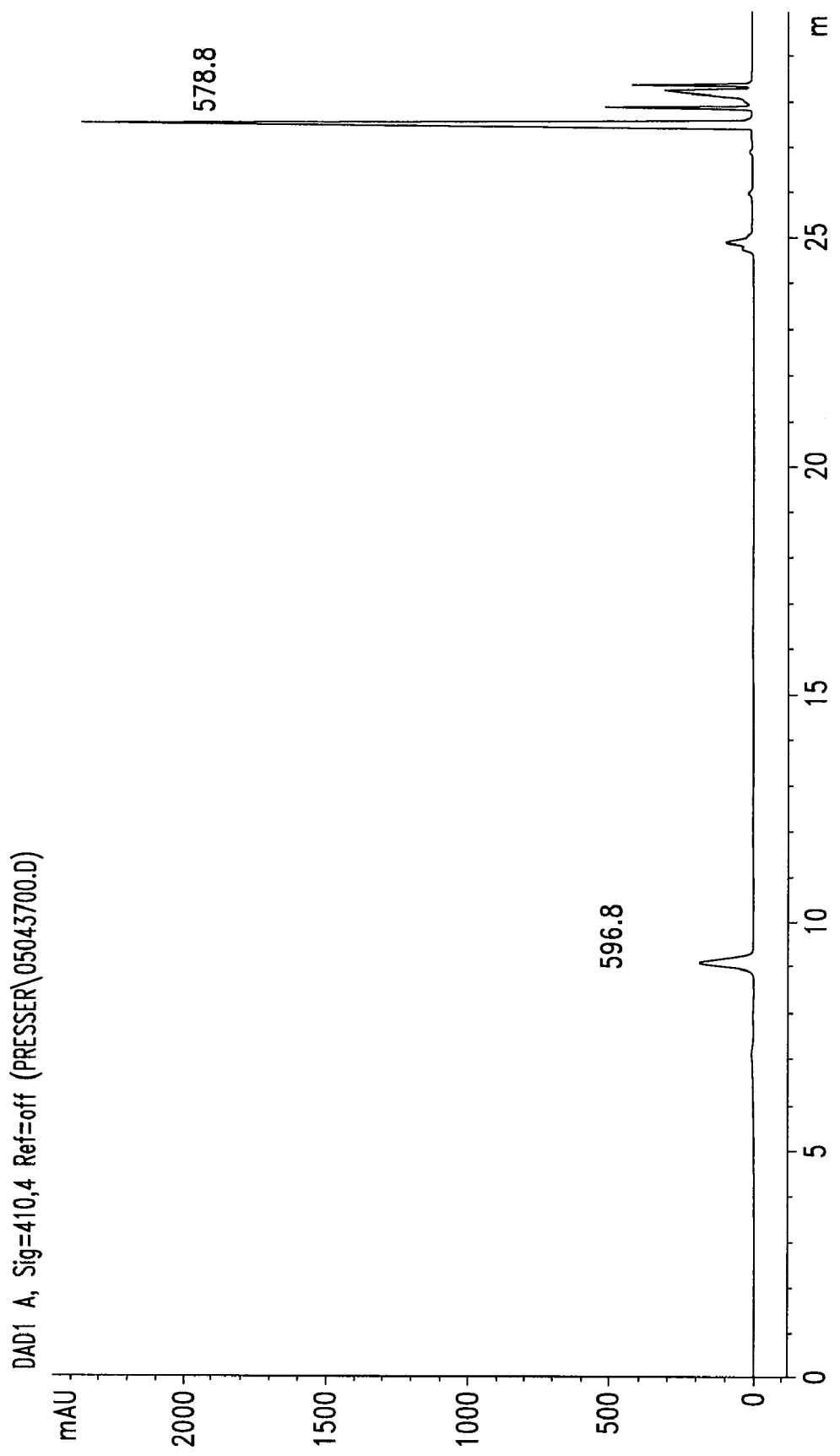
FIG. 2B is an absorbance (AU) at 410 nm versus time (min) HPLC (High Pressure Liquid Chromatography) plot of a chlorin $e_6$ anhydride composition according to one illustrative embodiment. The peaks labeled as 596.8 and 578.8 are chlorin $e_6$ and chlorin $e_6$ anhydride respectively.

In the following description, certain specific details are included to provide a thorough understanding of various disclosed embodiments. One skilled in the relevant art, however, will recognize that embodiments may be practiced without one or more of these specific details, or with other methods, components, materials, etc. In other instances, well-known structures associated with extraction, separation, chromatography, and/or purification systems including but not limited to separation columns, filtration beds, and the like, have not been shown or described in detail to avoid unnecessarily obscuring descriptions of the embodiments.

Unless the context requires otherwise, throughout the specification and claims which follow, the word "comprise" and variations thereof, such as, "comprises" and "comprising" are to be construed in an open, inclusive sense, that is as "including, but not limited to."

Reference throughout this specification to "one embodiment," or "an embodiment," or "in another embodiment," or "in some embodiments" means that a particular referent feature, structure, or characteristic described in connection with the embodiment is included in at least one embodiment. Thus, the appearance of the phrases "in one embodiment," or "in an embodiment," or "in another embodiment," or "in some embodiments" in various places throughout this specification are not necessarily all referring to the same embodiment. Furthermore, the particular features, structures, or characteristics may be combined in any suitable manner in one or more embodiments.

It should be noted that, as used in this specification and the appended claims, the singular forms "a," "an," and "the" include plural referents unless the content clearly dictates otherwise. Thus, for example, reference to a chemical reaction of a chlorin $e_6$ anhydride intermediate with an amine-containing reagent includes a single amine-containing reagent, or two or more amine-containing reagents. It should also be noted that the term "or" is generally employed in its sense including "and/or" unless the content clearly dictates otherwise.

The following detailed description is merely illustrative in nature and is not intended to limit the disclosure or the application and uses of the disclosure. Furthermore, there is no intention to be bound by any expressed or implied theory presented in the preceding technical field, background, brief summary or the following detailed description.

As used herein and in the claims, the term "dehydration agent" or "carboxyl activating agent" generally refers to a compound, molecule, or substance, capable of activating carboxylic acids with respect to nucleophilic attack. In some embodiments, the dehydration agents or carboxyl activating agents are capable of activating carboxylic acids where the attacking nucleophile is an amine or alcohol, resulting in amide or ester formation.

Non-limiting examples of such dehydration agents include carbodiimides (e.g., N,N'-dicyclohexylcarbodiimide (DCC), N,N'-diisopropylcarbodiimide, 1-ethyl-3-(3-dimethylaminopropyl)carbodiimide hydrochloride, and the like), cyanamides.

Further examples of dehydrating reagents include alkyl chloroformates (see e.g., Kim, Lee, Kim J. Org. Chem. 1985, 50, 560), which are generally used with a tertiary amine like triethyl amine, diethyl azodicarboxylate (DEAD) with triphenylphosphine (see e.g., Camp; Jenkins J. Org. Chem. 1989, 54, 3045, 3049 (the Mitsunobu Reaction)), various chlorosilanes (see e.g., Nakao; Oka; Fukumoto Bull. Chem. Soc. Jpn. 1981, 54, 1267; see also e.g., Brook; Chan, Synthesis 1983, 201), chlorosulfonyl isocyanate (see e.g., Dhar, Murthy Synthesis 1988, 437-450), and N,N'-carbonyldiimidazole (see e.g., Morton, Mangroo, Gerber Can. J. Chem. 1988, 66, 1701). In some embodiments, the dehydration agent is a carbodiimide. In some embodiments, the carbodiimide is N-ethyl-N'-(3-dimethylaminopropyl)-carbodiimide hydrochloride or N,N'-dicyclohexyl-carbodiimide.

In some embodiments, dehydration of the reactants may comprise a reaction of carboxylic acids with amines, whether or not they are part of amino acids. In some embodiments, more general ways of dehydrating the reactants in order to obtain the desired coupling reaction may be employed. (see e.g., Beckwith's monograph, pp. 73-185, in The Chemistry of Amides). For example, one general method is the reaction of an amine with an acid chloride. In some embodiments, the reactants are treated with chloroformates with primary amines, because this can be reversed later if the amine is needed for some purpose (see e.g., Zabicky, A. A., Ed.; Wiley: New York, 1970; Raucher; Jones Synth. Commun. 1985, 15, 1025.). As used herein and in the claims, the term "amine-containing agent" generally refers to a compound, molecule, or substance that contains a primary or secondary amine group, or ammonia. Non-limiting examples of such amine-containing agents include amino acids (e.g., L-aspartic acid), aspartic acid, and the like, or esters or derivatives thereof.

Talaporfin Sodium is commonly known as Mono-L-aspartyl-chlorin $e_6$, NPe$_6$, MACE, Taporfin, ME2906, Ace$_6$, AC$_6$ and LS11. Its Chemical Abstract Services Registry Number is 220201-34-3, and its chemical name is (+)-Tetrasodium (2S, 3S)-18-carboxylato-20-[N—(S)-1,2-dicarboxylatoethyl]-carbamoyl methyl-13-ethyl-3,7,12,17-tetramethyl-8-vinyl-chlorin-2-propanoate.

Talaporfin Sodium is a photosensitizing agent typically used in light activated drug therapy. After light activation, Talaporfin Sodium forms an extended high energy electronic state that facilitates the formation of singlet oxygen, resulting in singlet oxygen-mediated cell death. In some embodiments, when interacting with cancer cells and exposed to light, the Talaporfin Sodium may kill or destroy the cancer cells.

As shown in FIG. 1, producing Talaporfin, or a pharmaceutically acceptable salt thereof, from chlorin $e_6$ generally requires a two stage process. In some embodiments, in a first stage, chlorin $e_6$ is activated by dehydration agent, and in a second stage, an activation mixture reacts with an amine-containing agent to form Talaporfin Sodium.

Previously the reaction products of the activation step were thought to be unstable, high-energy, short-lived, species, and hence cannot be isolated or purified. Applicants have identified, however, a significant component of this reaction as the chlorin $e_6$ anhydride and unexpectedly found that this intermediate is a stable species. In some embodiments, when isolated or purified, the intermediate reacts with L-aspartate to form Talaporfin Sodium that is purer than the case if the isolation or purification of the chlorin $e_6$ anhydride had not taken place.

In some embodiments, the process for preparing Talaporfin, or a pharmaceutically acceptable salt thereof, may include combining chlorin $e_6$ with a carboxyl activating agent to obtain an activation reaction mixture comprising a Formula I intermediate

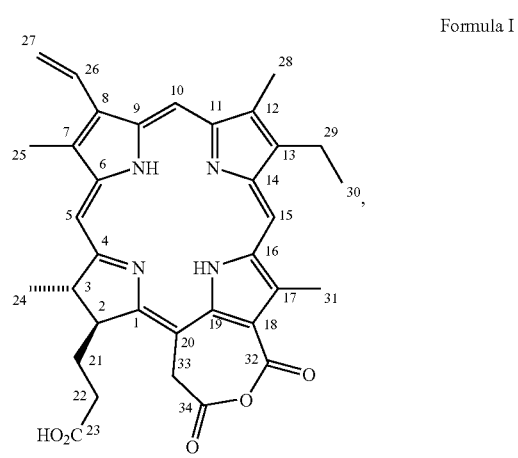

Formula I or a salt thereof.

Figure 5:
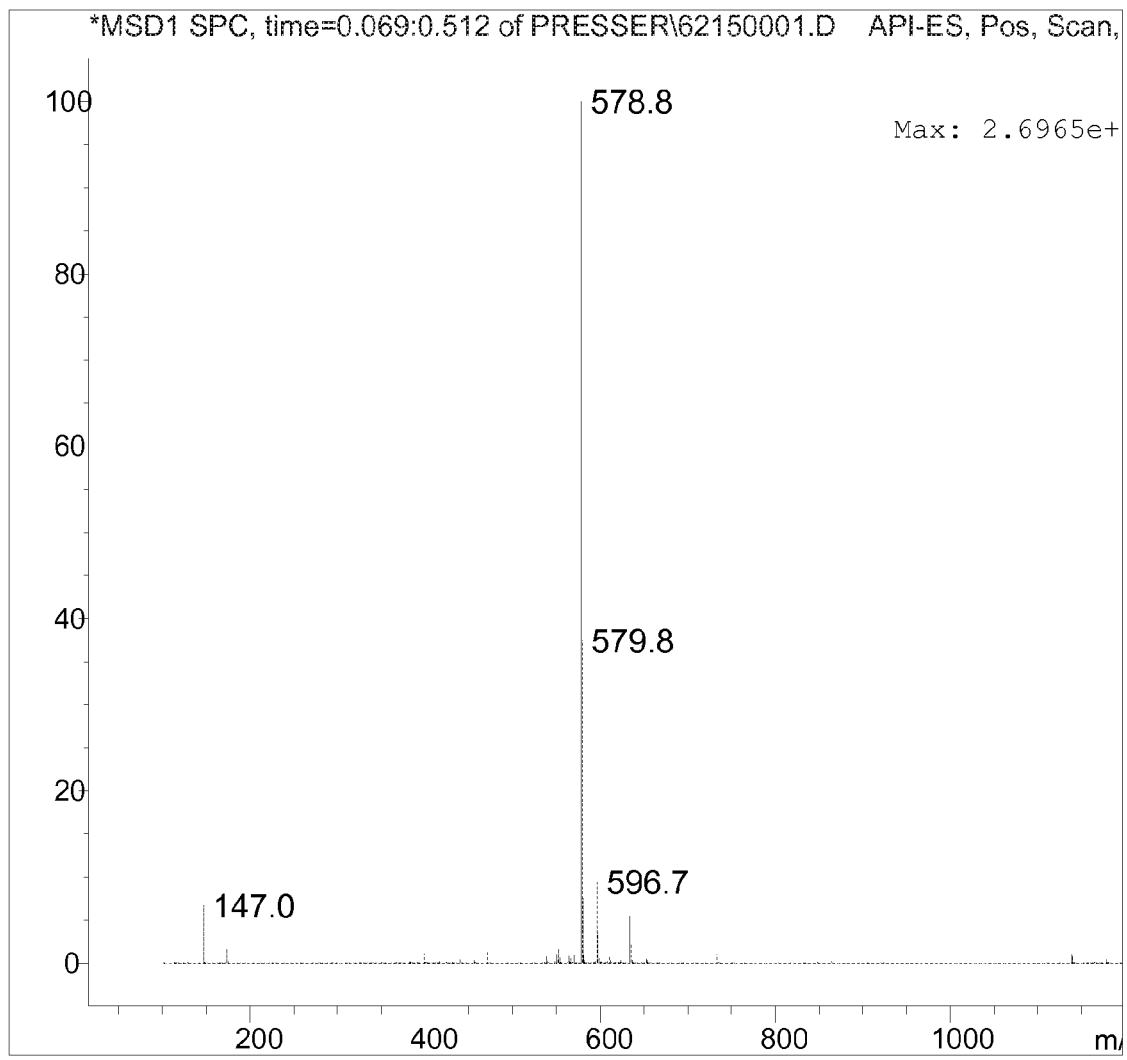
FIG. 5 is a relative intensity versus mass-to-charge ratio (m/z) mass spectrometry analysis plot of a reaction mixture resulting from an activation reaction, after treatment with activated silica, illustrating that the predominant species in the mixture is the chlorin $e_6$ anhydride according to one illustrative embodiment.

The process may further include isolating the Formula I intermediate, or salt thereof, from a reaction mixture using one or more separation. Suitable techniques and/or methods for extracting, isolating, separating, and/or purifying the Formula I intermediate, or salt thereof, from the mixture include extraction, separation, chromatography, and/or purification techniques such as liquid chromatography (e.g., HPLC), column chromatography, thin layer chromatography, planar chromatography, and the like. In some embodiments, the mixture may be passed through an activated silica bed, and the resultant silica-treated reaction product analyzed by mass spectrometry. FIG. 5 shows a mass spectrum for silica-treated reaction product following an activation reaction of chlorin $e_6$ by a dehydration agent. The spectrum was recorded on an Agilent 1100 series LC/MSD instrument using electrospray ionization and with polarity setting on positive.

As shown in FIG. 5, the peak for the chlorin $e_6$ anhydride is now proportionately much higher than those for the reaction byproducts. The most intense peak is that of the chlorin $e_6$ anhydride.

Figure 6:
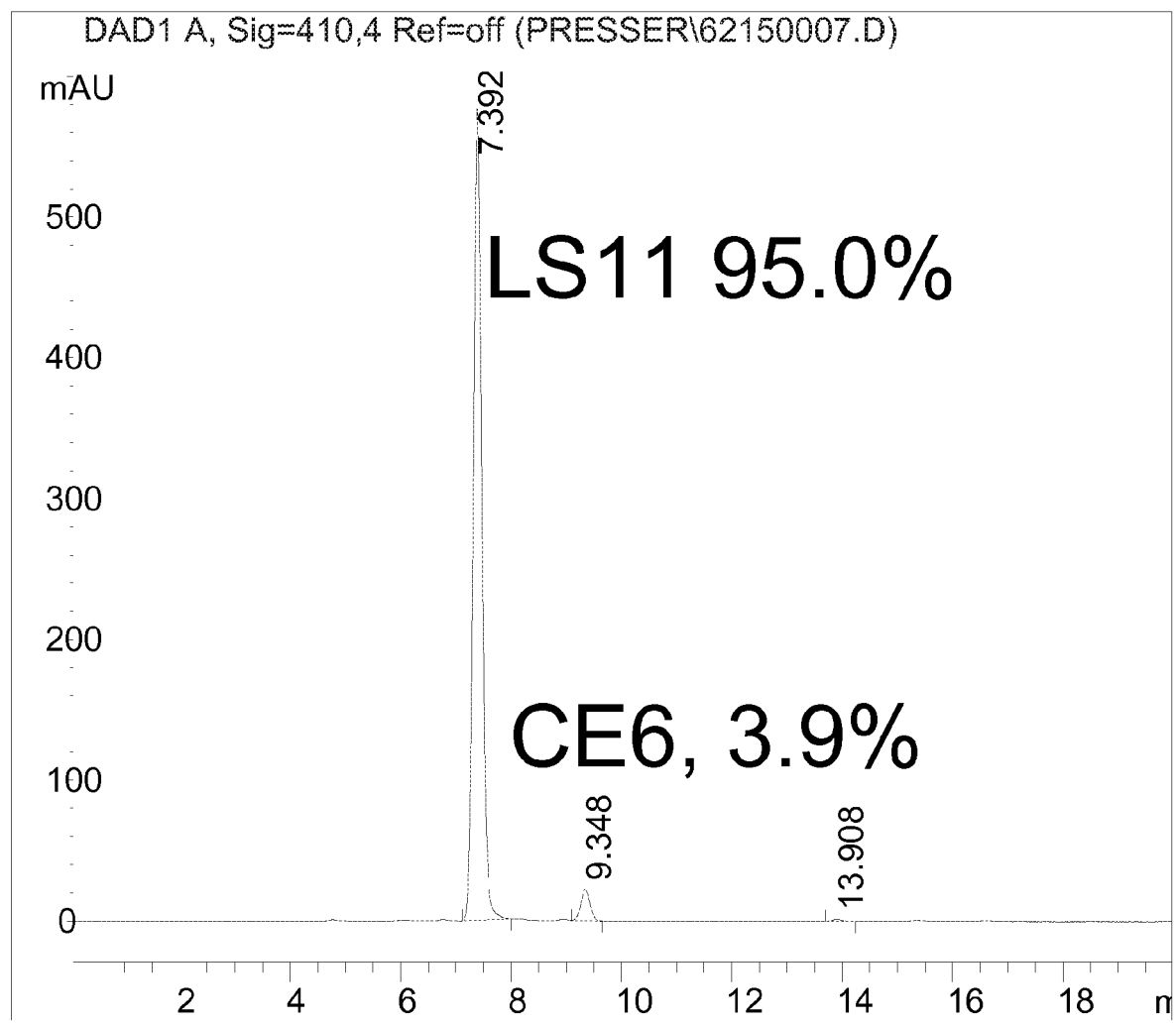
FIG. 6 is an absorbance (AU) at 410 nm versus time (min) HPLC plot using UV detection indicating the relative percentage of chlorin species present in a purified reaction product according to one illustrative embodiment.

When the silica-treated or otherwise purified activation reaction product, now containing a higher chlorin $e_6$ anhydride concentration, was allowed to react with L-aspartic acid in aqueous alkaline (sodium hydroxide was used to create alkaline conditions) solution a much purer Talaporfin Sodium-containing reaction product was produced, as compared to the prior art. The HPLC analysis of the coupling reaction product is shown in FIG. 6. It shows that about 95% of the coupling reaction product (based on total chlorin species present), is Talaporfin Sodium with only about 5% other reaction products. This coupling reaction product is much simpler and less costly to purify further to 96% Talaporfin Sodium than the reaction product of the prior art that had a much lower proportion of Talaporfin Sodium. In some embodiments, the resulting Talaporfin Sodium comprises a purity greater than from about 90% to about 99% or greater.

The purification of the coupling reaction product requires a series of treatments with HPLC to remove impurities. Consequently, in some embodiments, starting the purification process with a reaction product that has a higher Talaporfin Sodium concentration (and reduced concentrations of other (unwanted) activation reaction products, such as precursors of diaspartyl chlorin $e_6$) also offers the potential for eliminating the need for HPLC purification processes. Accordingly, some embodiments offer the potential for higher Talaporfin Sodium yields, as well as higher Talaporfin Sodium purity.

Figure 3:
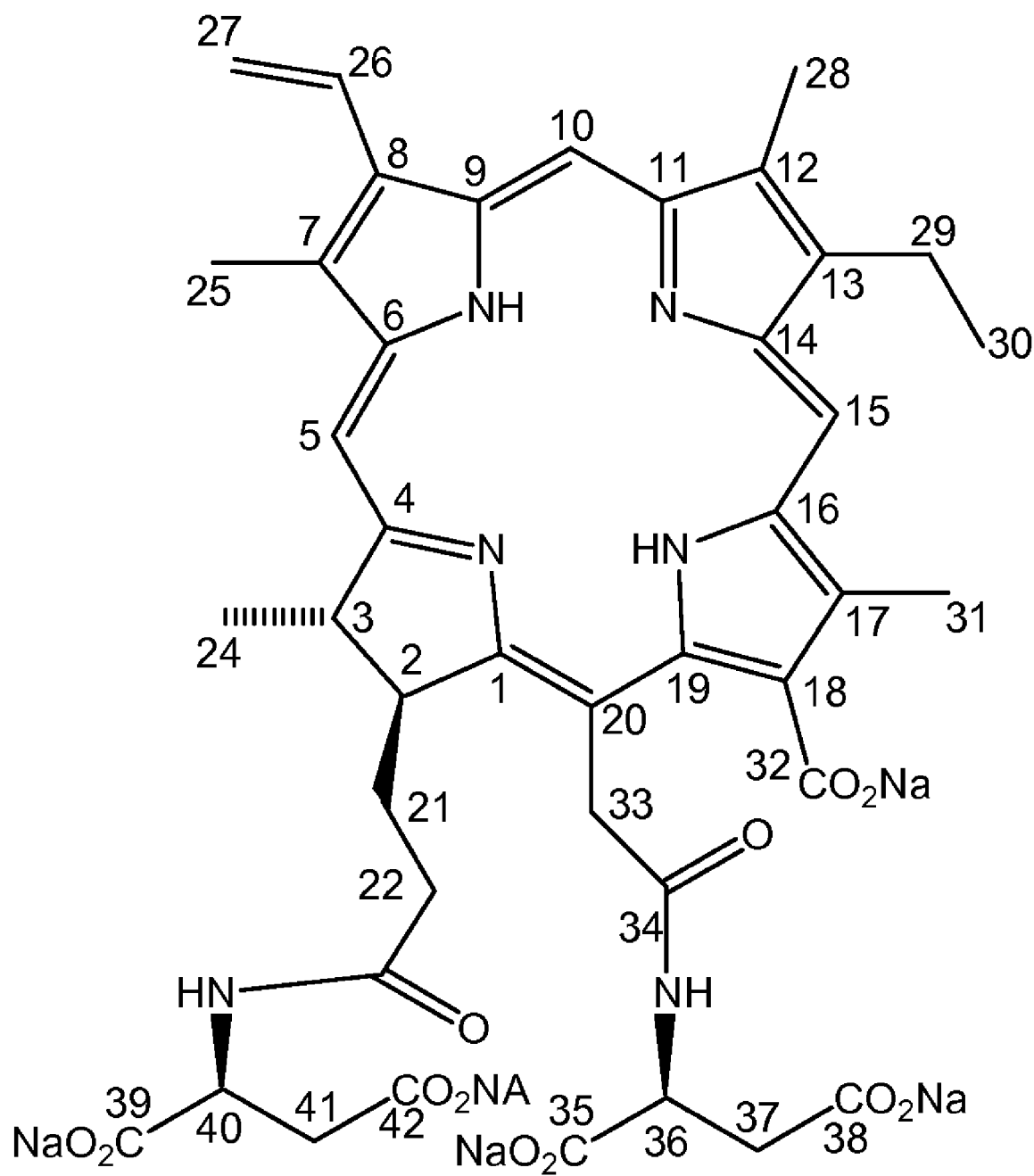
FIG. 3 is a schematic depiction of a structural formula of one isomer of di-L-aspartyl chlorin $e_6$ according to one illustrative embodiment.

In some embodiments, the activation reaction mixture produced from the activation reaction is first purified to produce a purified activation reaction mixture that has an enhanced concentration of the chlorin $e_6$ anhydride, and reduced concentrations of other (unwanted) activation reaction products, such as precursors of diaspartyl chlorin $e_6$ (a drawing of one isomer of diaspartyl chlorin $e_6$ is shown in FIG. 3). Di-L-aspartyl chlorin $e_6$ typically comprises 3-4% of the total product mixture. Generally, diaspartyl chlorin $e_6$ is removed by multiple stages in series of reverse phase HPLC steps. The HPLC process employed, however, is both expensive and time consuming. Moreover, multiple stage HPLC separation results in loss of Talaporfin Sodium product, thereby reducing product yield by as much as 50%.

It has now been found that there is an "activated intermediate" heretofore unsuspected in the activation mixture, having the following Formula I structure:

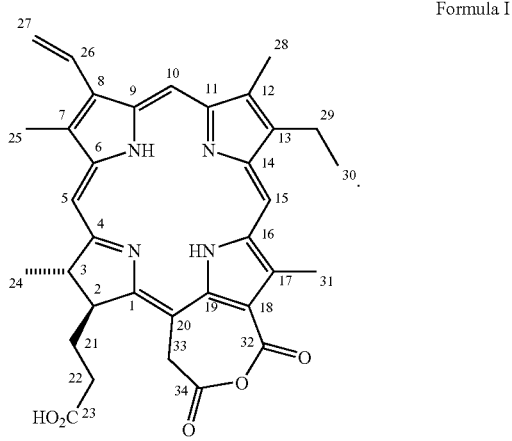

Formula I

Figure 4:
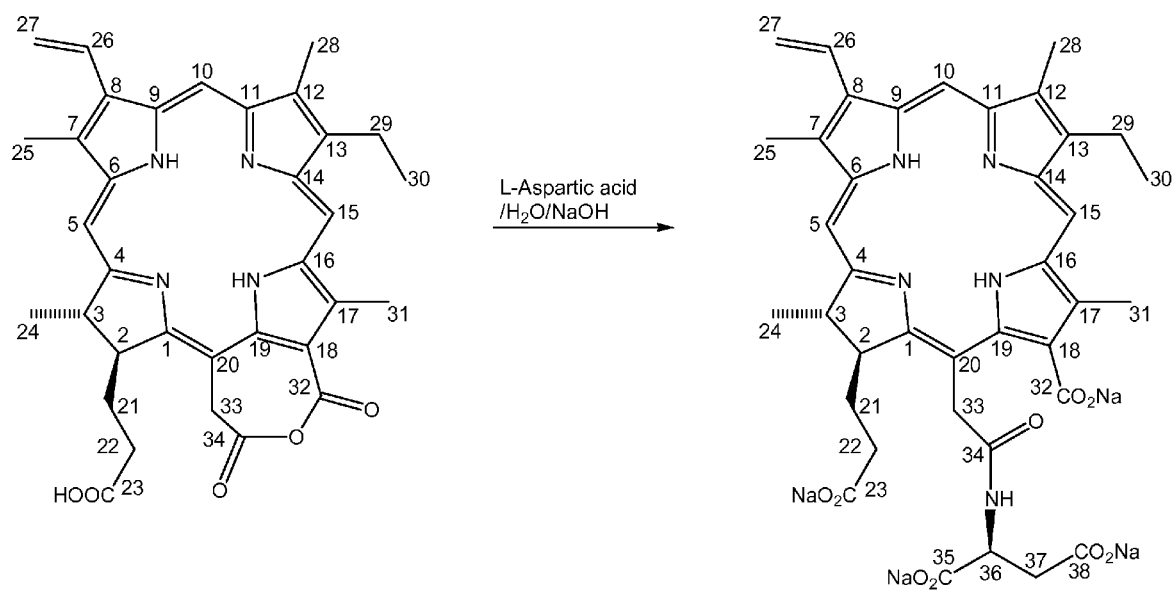
FIG. 4 is a schematic depiction of isolated chlorin $e_6$ anhydride conversion to Talaporfin Sodium according to one illustrative embodiment.

This Formula I chlorin $e_6$ anhydride may be referred to as "chlorin $e_6$ cyclic anhydride," or "anhydride." When this chlorin $e_6$ anhydride, purified from the activation mixture, is allowed to react in the coupling reaction with L-aspartyl chlorin $e_6$, as shown in FIG. 4, the production of diaspartyl chlorin $e_6$ is dramatically reduced.

In some embodiments, the process may further include combining the isolated Formula I intermediate, or salt thereof, with an amine-containing reagent to form Talaporfin Sodium, or a pharmaceutically acceptable salt thereof. In some embodiments, combining chlorin $e_6$ with the carboxyl activating agent comprises reacting chlorin $e_6$ with a carbodiimide. In some embodiments, the carbodiimide is DCC or EDC.

In some embodiments, combining chlorin $e_6$ with the carboxyl activating agent comprises combining the chlorin $e_6$ with a carbodiimide in the presence of dimethyl sulfoxide or dimethyl formamide. In some embodiments, combining the chlorin $e_6$ with the carboxyl activating agent comprises combining the chlorin $e_6$ with EDC or DCC.

In some embodiments, isolating the Formula I intermediate, or salt thereof, comprises separating the Formula I intermediate, or salt thereof, from the mixture by using activated silica to yield a substantially pure Formula I intermediate, or salt thereof.

In some embodiments, combining the isolated Formula I intermediate, or salt thereof, with an amine-containing reagent comprises combining the isolated Formula I intermediate, or salt thereof, with sodium aspartate to form Talaporfin Sodium.

In some embodiments, combining the isolated Formula I intermediate, or salt thereof, with an amine-containing reagent comprises combining the isolated Formula I intermediate, or salt thereof, in the presence of dimethyl sulfoxide, with L-aspartic acid or ester thereof to form Talaporfin Sodium.

In some embodiments, combining the isolated Formula I intermediate, or salt thereof, with an amine-containing reagent comprises coupling the chlorin $e_6$ anhydride to L-aspartic acid or ester thereof in an aqueous alkaline solution to form a tetra-sodium salt of mono-L-aspartyl chlorin $e_6$.

Certain embodiments of the present disclosure are directed to a process for preparing a chlorin $e_6$ anhydride, or a pharmaceutically acceptable salt thereof. The process includes combining chlorin $e_6$ with a carboxyl activating agent to obtain a mixture comprising a chlorin $e_6$ anhydride having the following formula

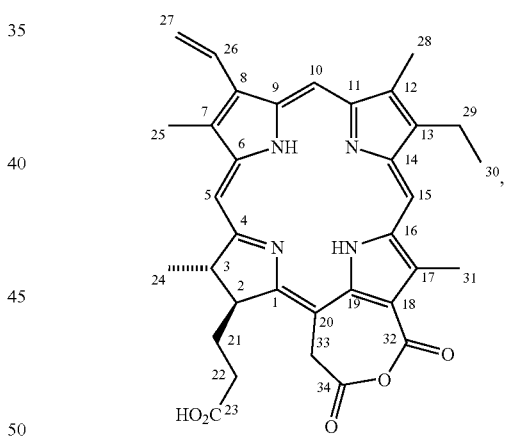

or a salt thereof.

In some embodiments, the carboxyl activating agent is DCC or EDC.

The process may further includes purifying the chlorin $e_6$ anhydride, or salt thereof. In some embodiments, purifying the chlorin $e_6$ anhydride, or salt thereof, comprises isolating the chlorin $e_6$ anhydride, or salt thereof, from the mixture using one or more extraction, separation, chromatography, and/or purification techniques.

Figure 7:
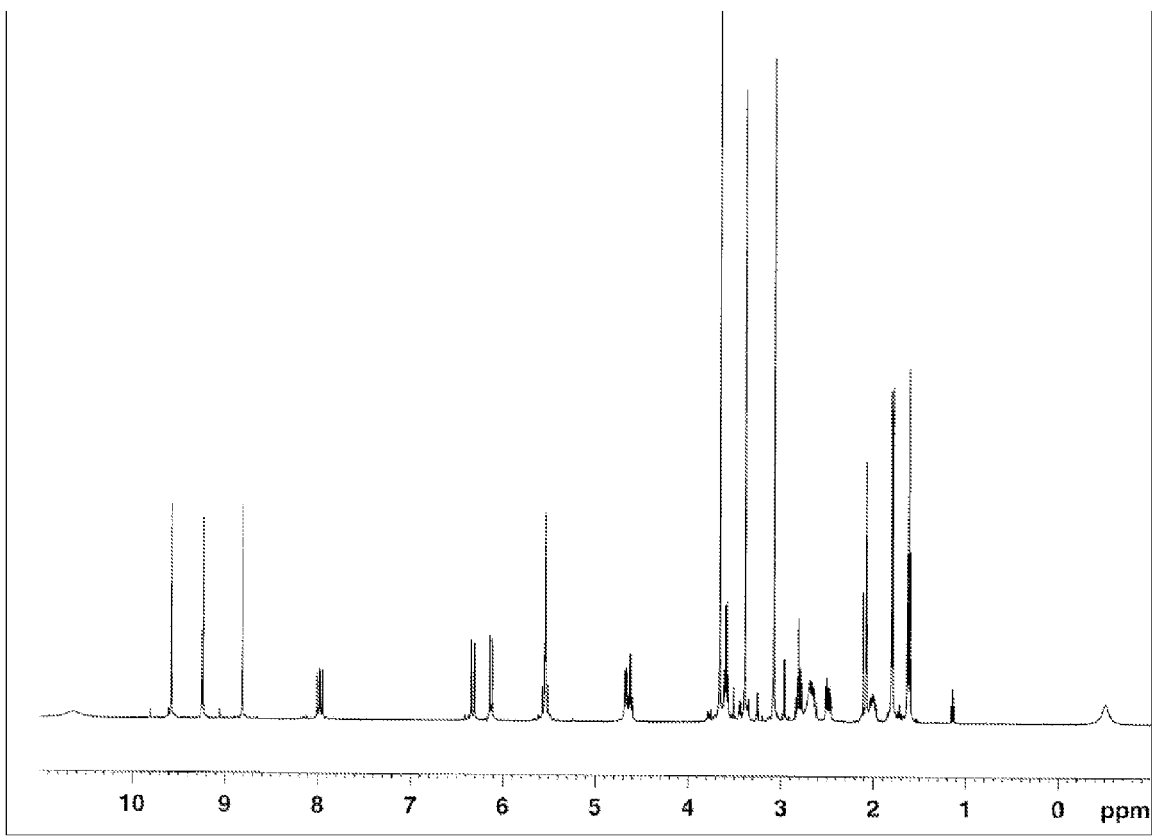
FIG. 7 is a proton nuclear magnetic resonance ($^1$H-NMR) spectrum of chlorin $e_6$ anhydride in $d_6$-acetone/$d_6$-dimethyl sulfoxide, taken at 500 MHz according to one illustrative embodiment.

FIG. 7 shown an $^1$H NMR spectrum of chlorin $e_6$ anhydride in acetone $d_6$ according to one illustrative embodiment. Referring to TABLE 1, the position assignments are numbered according to the corresponding atoms as indicated by the following Formula I chlorin $e_6$ anhydride

TABLE 1

1H NMR Peak Assignments

Formula I

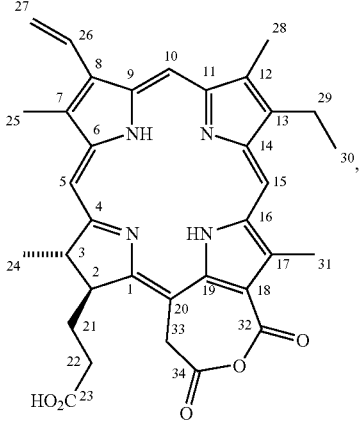

| Position Assignment | δ(ppm) Chemical Shift (ppm) | M Multiplicity | J (Hz) J (Hz) |
|---|---|---|---|
| 2 | 4.67 | br d | 10.7/2.0 |
| 3 | 4.63 | br q | 7.3 |
| 5 | 9.35 | s | |
| 10 | 8.86 | s | |
| 15 | 9.67 | s | |
| 21 | 1.72/2.05 | m | |
| 22 | 2.50/2.65 | m | |
| 24 | 1.78 | d | 7.3 |
| 25 | 3.42 | s | |
| 26 | 8.07 | dd | 17.9/11.5 |
| 27 | 6.37/6.16 | d | 17.9/11.5 |
| 28 | 3.14 | s | |
| 29 | 3.68 | br q | 7.7 |
| 30 | 1.63 | t | 7.7 |
| 31 | 3.69 | s | |
| 33 | 5.59/5.56 | d | 13.7 |

Figure 8:
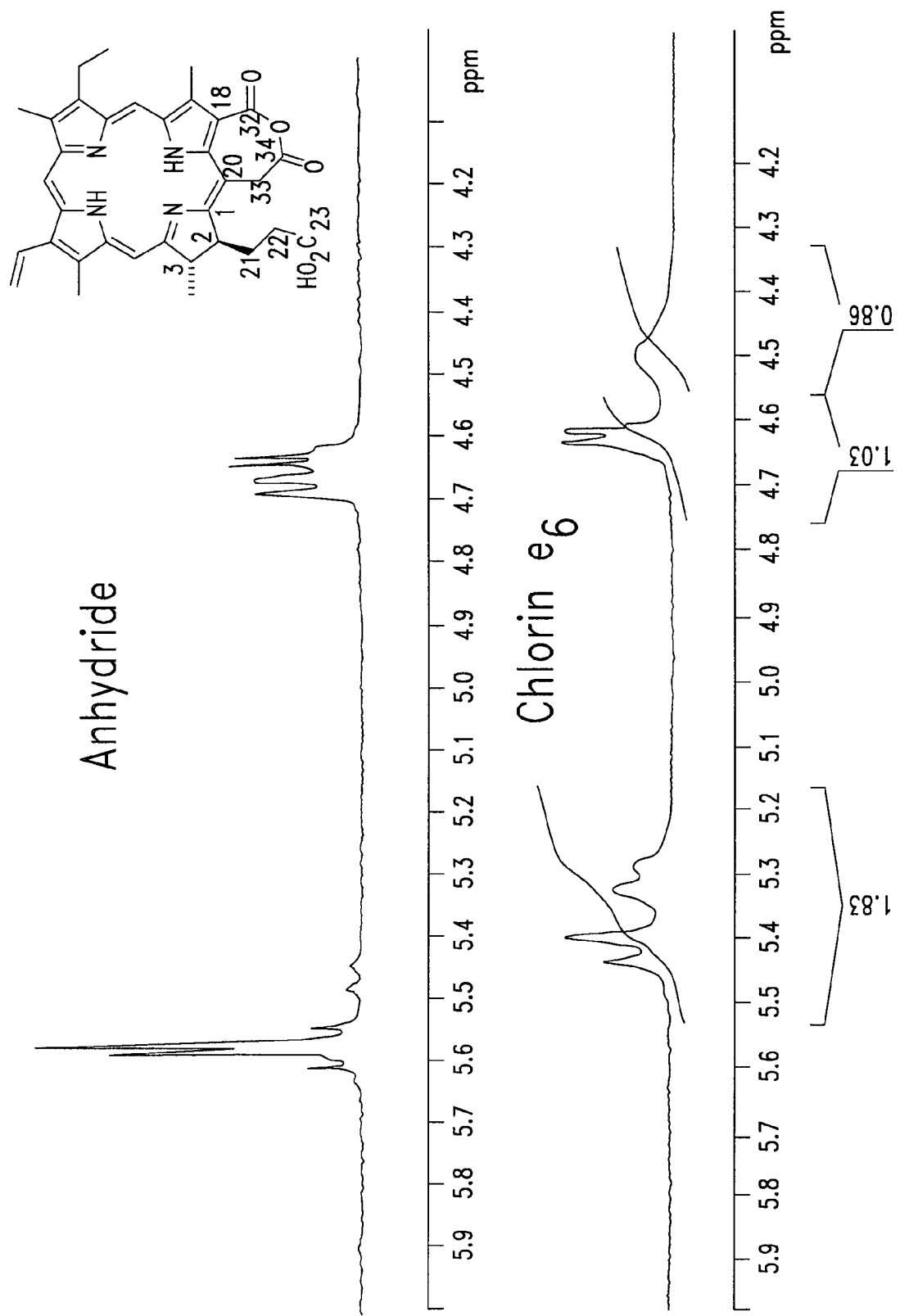
FIG. 8 is comparison of a select region of an $^1$H-NMR spectrum of chlorin $e_6$ anhydride in $d_6$-acetone/$d_6$-dimethyl sulfoxide, and a select region of an $^1$H-NMR spectrum of chlorin $e_6$ in $d_6$-acetone/$d_6$-dimethyl sulfoxide, taken at 500 MHz according to one illustrative embodiment.

FIG. 8 shows a 4-6 ppm expanded portion of the NMR spectrum in FIG. 7, as well as a 4-6 ppm expanded portion of an NMR spectrum of chlorin $e_6$ taken under similar conditions. The plots evidence some of the structural difference between chlorin $e_6$ and the anhydride.

Certain embodiments of the present disclosure are directed to a method for preparing an intermediate. The method includes activating chlorin $e_6$ with a carboxyl activating agent to obtain a mixture including an intermediate, the intermediate exhibiting a spectrum comprising chemical shifts in ppm at about 1.63 (t, 3H), 1.72/2.05 (m, 2H), 1.78 (d, 3H), 2.50/2.65 (m, 2H), 3.14 (s, 3H), 3.42 (s, 3H), 3.68 (br. q, 2H), 3.69 (s, 3H), 4.63 (br. q, 1H), 4.67 (br. d, 1H), 5.59/5.56 (d, 2H), 6.37/6.16 (d, 1H), 8.07 (dd, 1H), 8.86 (s, 1H), 9.35 (s, 1H), and 9.67 (s, 1H) when analyzed using proton nuclear magnetic resonance ($^1$H-NMR) spectroscopy, at 500 MHz, using $d_6$-acetone/$d_6$-dimethyl sulfoxide as a solvent.

The method further includes isolating the intermediate. In some embodiments, isolating the intermediate comprises separating the intermediate from the mixture using one or more extraction, separation, chromatography, and/or purification techniques. In some embodiments, the one or more extraction, separation, chromatography, and/or purification techniques includes contacting the mixture with activated silica.

The method may further include drying the isolated intermediate in the presence of a vacuum.

Certain embodiments of the present disclosure are directed to a method for preparing Talaporfin, or a salt thereof. The method includes combining an intermediate (prepared by combining chlorin $e_6$ with a carboxyl activating agent to obtain a mixture comprising a chlorin $e_6$ anhydride having the following formula

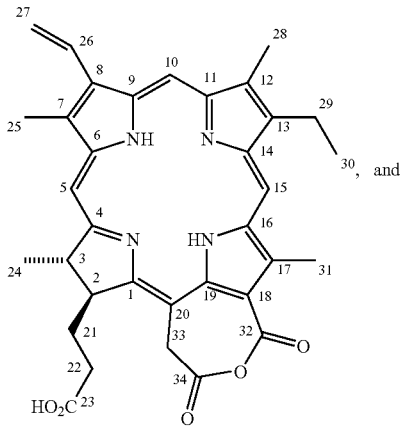

or a salt thereof,
and purifying the chlorin $e_6$ anhydride, or salt thereof) with an amine-containing reagent to form a mono amino acid chlorin $e_6$, or a pharmaceutically acceptable salt thereof. In some embodiments, the amine-containing reagent is L-aspartic acid or an ester thereof.

Certain embodiments of the present disclosure are directed to a reaction product. The reaction comprises a product of a coupling reaction between a first reaction volume and a second reaction volume, the first reaction volume comprising a chlorin $e_6$ anhydride of the formula and less than about 5 mol % precursors of diaspartyl chlorin $e_6$ based on total chlorin species present in the first reaction volume; and the second reaction volume comprising L-aspartic acid or ester thereof. In some embodiments, the units mol % and % AUC (area under the curve) are used interchangeably. % AUC is defined as percent area under curve and is determined by HPLC-UV absorbance analysis using a detection signal having wavelength of about 400 nm or about 410 nm. % AUC is calculated by dividing area under curve of the peak of interest by area under curve of all peaks in the chromatogram. In some embodiments, % AUC is expected to be proportional to the concentration of the chlorin species in the mixture as they share the same chromophore. Accordingly, by measuring the % AUC of the separated species in an HPLC chromatogram, it is possible to determine the relative concentration and/or mol % of species present in a reaction mixture. In some embodiments, the relative AUC for the respective HPLC plot peaks may be use to determine the relative concentration and/or mol % of species present in a reaction mixture.

In some embodiments, the reaction product comprises mono-L-aspartyl chlorin $e_6$, or a pharmaceutically acceptable salt thereof, and diaspartyl chlorin $e_6$. In some embodiments, the reaction product comprises less than about 2 mol % diaspartyl chlorin $e_6$ based on total chlorin species present in the reaction product. In some embodiments, the reaction product comprises less than about 1 mol % diaspartyl chlorin $e_6$ based on total chlorin species present in the reaction product. In some embodiments, the first reaction volume further comprises dimethyl sulfoxide or dimethyl formamide.

The first reaction volume can be purified to remove precursors of diaspartyl chlorin $e_6$ by a separation process. In some embodiments, the separation process is activated silica chromatography. In some embodiments, the resulting activation mixture is combined with L-aspartic acid (as shown in FIG. 4) in an alkaline aqueous solution to yield Talaporfin Sodium among other byproducts.

Certain embodiments of the present disclosure are directed to a chemical reaction product of chlorin $e_6$ and a carbodiimide, the chemical reaction product comprising a chlorin $e_6$ anhydride of the form:

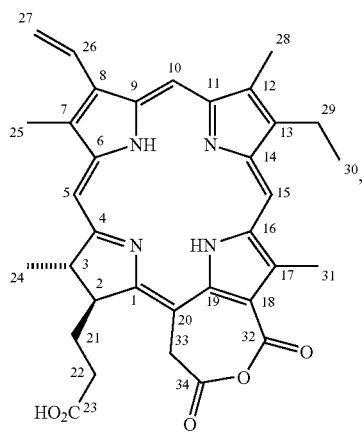

and precursors of diaspartyl chlorin $e_6$.

In some embodiments, the precursors of diaspartyl chlorin $e_6$ comprise less than about 5 mol % of a total chlorin species present within the chemical reaction product. In some further embodiments, the precursors of diaspartyl chlorin $e_6$ comprise less than about 3 mol % of total chlorin species present within the chemical reaction product. In some embodiments, the chlorin $e_6$ anhydride comprises at least about 85 mol % of the total chlorin species present within the chemical reaction product.

In some embodiments, the carbodiimide is EDC or DCC.

Certain embodiments of the present disclosure are directed to a composition comprising a compound of Formula I

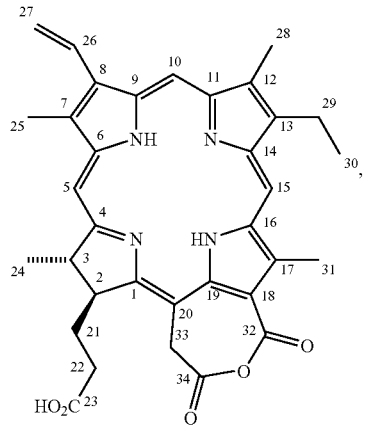

(Formula I)

or a pharmaceutically acceptable salt thereof, in a substantially pure form.

In some embodiments, the total content of the Formula I compound, or a pharmaceutically acceptable salt thereof, is greater than about 85 mol % of total chlorin species within the composition. In some embodiments, the total content of the Formula I compound, or a pharmaceutically acceptable salt thereof, is greater than about 90 mol % of total chlorin species within the composition. In some embodiments, the total content of the Formula I compound, or a pharmaceutically acceptable salt thereof, is greater than about 95 mol % of total chlorin species within the composition.

In some embodiments, the total content of the Formula I compound, or a pharmaceutically acceptable salt thereof, is greater than about 85 wt % of the composition. In some embodiments, the total content of the Formula I compound, or a pharmaceutically acceptable salt thereof, is greater than about 90 wt % of the composition. In some embodiments, the total content of the Formula I compound, or a pharmaceutically acceptable salt thereof, is greater than about 95 wt % of the composition.

Certain embodiments of the present disclosure are directed to a chemical reaction product comprising a compound of Formula I

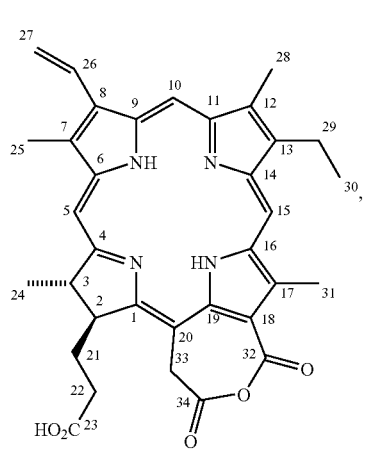

(Formula I)

or a pharmaceutically acceptable salt thereof, in a substantially pure form.

In some embodiments, the total content of the Formula I compound is greater than about 85 mol % based on the total amount of chlorin species present within the chemical reaction product. In some embodiments, the total content of the Formula I compound is greater than about 90 mol % based on the total amount of chlorin species present within the chemical reaction product. In some embodiments, the total content of the Formula I compound is greater than about 95 mol % based on the total amount of chlorin species present within the chemical reaction product.

Certain embodiments of the present disclosure are directed to a method for preparing Talaporfin Sodium, or a pharmaceutically acceptable salt thereof. The method includes combining an aspartate salt composition having a pH ranging from about 8 to about 12 with a chemical reaction product of chlorin e$_6$ and a carbodiimide the presence of an organic solvent to form a reaction mixture. In some embodiments, the organic solvent is selected from dimethyl formamide, dimethyl sulfoxide, tetrahydrofuran, ethyl acetate, methylene chloride, or mixtures thereof.

In some embodiments, the chemical reaction product comprises a chlorin e$_6$ anhydride of the form:

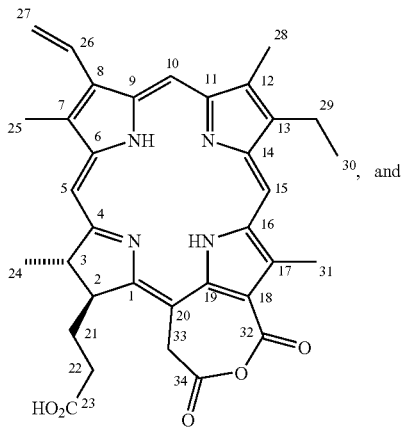

, and precursors of diaspartyl chlorin e$_6$. In some embodiments, the precursors of diaspartyl chlorin e$_6$ comprise less than about 5 mol % based on the total amount of chlorin species present within the chemical reaction product.

The method may further include rendering the reaction mixture basic. In some embodiments, rendering the reaction mixture basic comprises adding hydroxide to maintain a pH of the reaction mixture at about 8 to about 12.

In some embodiments, the method may further include precipitating the Talaporfin, or a pharmaceutically acceptable salt thereof, from the basic reaction mixture. In some embodiments, precipitating the Talaporfin, or a pharmaceutically acceptable salt thereof, comprises adding a suitable precipitation solvent to the basic reaction mixture.

The method may further include separating the Talaporfin (or a pharmaceutically acceptable salt thereof) precipitate from the basic reaction mixture by filtration, centrifugation, and/or chromatography.

Certain embodiments of the present disclosure are directed to a method of preparing Talaporfin Sodium. The method includes utilizing a purified intermediate reaction mixture in a reaction to prepare Talaporfin Sodium, the purified intermediate reaction mixture having been obtained from a crude reaction mixture comprising chlorin e$_6$, a chlorin e$_6$ anhydride, and precursors of diaspartyl chlorin e$_6$ from which a significant proportion of the precursors of diaspartyl chlorin e$_6$ has been removed.

In some embodiments, the purified intermediate reaction mixture comprises less than about 5% precursors of diaspartyl chlorin e$_6$ based on total chlorin species. In some embodiments, the purified intermediate reaction mixture comprises less than about 3 mol % precursors of diaspartyl chlorin e$_6$ based on total chlorin species.

In some embodiments, the chlorin e$_6$ cyclic anhydride is a Formula I chlorin e$_6$ cyclic anhydride

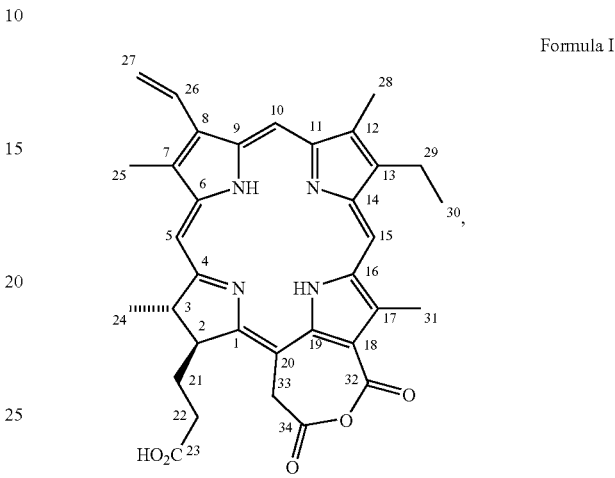

or salt thereof.

In some embodiments, the purified intermediate reaction mixture further comprises dimethyl sulfoxide. In some embodiments, the purified intermediate reaction mixture further comprises EDC or DCC and dimethyl formamide. In some embodiments, a significant proportion of the precursors of diaspartyl chlorin e$_6$ has been removed by using activated silica.

Certain embodiments of the present disclosure are directed to a process for preparing a photoactive agent, or a pharmaceutically acceptable salt thereof. The process include combining a composition comprising a compound of the formula

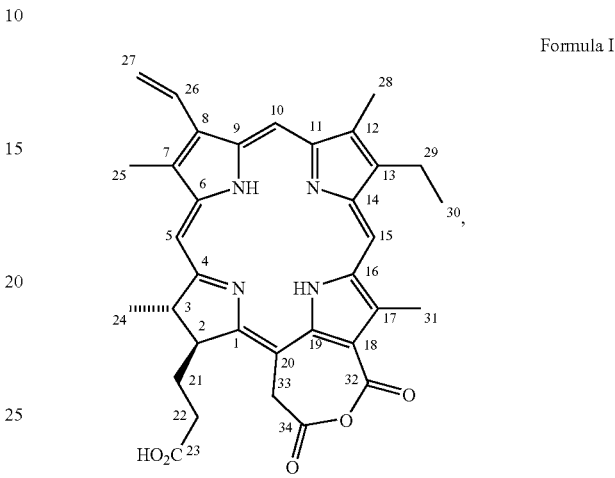

or a pharmaceutically acceptable salt
thereof, an organic solvent, and one or more of diaspartyl chlorin e$_6$ precursors, with a basic aqueous sodium aspartate composition to form a crude mono-L-aspartyl chlorin e$_6$ reaction mixture, the crude reaction mixture comprising less than about 2 mol % diaspartyl chlorin e$_6$ based on total chlorin species present within the crude reaction mixture The process may further include making the reaction mixture basic. The process may further include precipitating a substantial amount of the mono-L-aspartyl chlorin $e_6$ from the reaction mixture. In some embodiments, precipitating a substantial amount of the mono-L-aspartyl chlorin $e_6$ from the reaction mixture comprises providing a sufficient amount of an organic solvent to cause the precipitation of more than about 50 mol % of the mono-L-aspartyl chlorin $e_6$ present from the reaction mixture.

In some embodiments, making the reaction mixture basic comprises providing a sufficient amount of an alkaline agent to the reaction mixture to maintain a pH range from about 8 to about 12. In some embodiments, making the reaction mixture basic comprises providing a sufficient amount of an alkaline agent to the reaction mixture to maintain a pH range from about 10 to about 12.

In some embodiments, the at least one diaspartyl chlorin $e_6$ precursor comprises from less than about 1 mol % to about 2 mol % of the total chlorin species present in the reaction mixture.

Certain embodiments of the present disclosure are directed to a reaction product comprising a chlorin $e_6$ anhydride of the form:

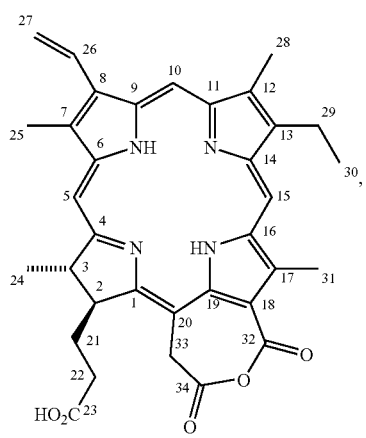

and precursors of diaspartyl chlorin $e_6$; wherein the precursors of diaspartyl chlorin $e_6$ comprise less than about 1 to 2 mol % of the total chlorin species present.

Example 1

Chlorin E$_6$ Anhydride Synthesis

Chlorin $e_6$ (2.0 g, 3.3 mmol) (Frontier Scientific) was dissolved in 10 mL DMF. EDC (0.61 g, 3.2 mmol) was added to the mixture and allowed to react for 1.5 h. The reaction mixture was loaded onto a bed of silica gel (Sigma-Aldrich) and eluted with acetone. The colored portion was collected and concentrated in vacuo. The anhydride was further dried in the presence of a vacuum.

Example 2

Talaporfin Sodium Synthesis

A sodium aspartate solution was prepared by adding 10 M NaOH to aspartic acid (~1.3 g, 10 mmol) in 10 mL water until pH 11 was attained. Chlorin $e_6$ anhydride from EXAMPLE 1 was dissolved in DMF and added slowly to the sodium aspartate solution. The mixture was made basic with 10M NaOH. Excess DMF was added to the dark suspension to precipitate the product. The product was collected by filtration and washed with acetone. The material was re-suspended in acetone and collected by filtration. The resultant crude Talaporfin Sodium was dried in the presence of a vacuum.

While at least one example embodiment has been presented in the foregoing detailed description, it should be appreciated that a vast number of variations exist. It should also be appreciated that the example embodiment or embodiments described herein are not intended to limit the scope, applicability, or configuration of the disclosure in any way. Rather, the foregoing detailed description will provide those skilled in the art with a convenient road map for implementing the described embodiment or embodiments. It should be understood that various changes can be made in the function and arrangement of elements without departing from the scope of the disclosure as set forth in the appended claims and the legal equivalents thereof.

What is claimed is:

1. A composition, comprising a compound of Formula I:

Formula I

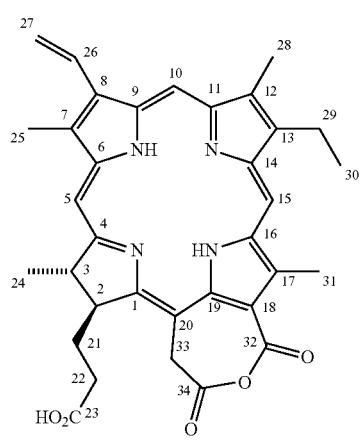

or a pharmaceutically acceptable salt or ester thereof and at least one other chlorin species.

2. The composition of claim 1 wherein a total content of the Formula I compound, or a salt or ester thereof, is greater than about 85 wt % of the composition or 85 mol % based on the total amount of chlorin species present.

3. The composition of claim 1 wherein a total content of the Formula I compound, or a salt or ester thereof, is greater than about 90 wt % of the composition or 90 mol % based on the total amount of chlorin species present within the composition.

4. The composition of claim 1 wherein a total content of the Formula I compound, or a salt or ester thereof, is greater than about 95 wt % of the composition or 95 mol % based on the total amount of chlorin species present within the composition.

* * * * *